United States Patent
Huang

(10) Patent No.: US 10,778,914 B2
(45) Date of Patent: Sep. 15, 2020

(54) PORTABLE MULTISPECTRAL IMAGING DEVICE AND METHOD OF REDUCING INTERFERENCE OF DISPLAYED IMAGES THEREOF

(71) Applicant: EXPANTRUM OPTOELECTRONICS, Shanghai (CN)

(72) Inventor: Zhongshou Huang, Shanghai (CN)

( * ) Notice: Subject to any disclaimer, the term of this patent is extended or adjusted under 35 U.S.C. 154(b) by 301 days.

(21) Appl. No.: 15/871,128

(22) Filed: Jan. 15, 2018

(65) Prior Publication Data

US 2018/0279967 A1 Oct. 4, 2018

(30) Foreign Application Priority Data

Mar. 30, 2017 (CN) .......................... 2017 1 0202019
Mar. 30, 2017 (CN) .......................... 2017 1 0202248

(51) Int. Cl.

| H04N 5/33 | (2006.01) |
|---|---|
| H04N 5/369 | (2011.01) |
| H04N 5/225 | (2006.01) |
| H01L 27/146 | (2006.01) |
| A61B 5/00 | (2006.01) |

(Continued)

(52) U.S. Cl.
CPC ........... *H04N 5/332* (2013.01); *A61B 5/0035* (2013.01); *A61B 5/0075* (2013.01); *A61B 5/0077* (2013.01); *A61B 5/1032* (2013.01); *A61B 5/489* (2013.01); *A61B 5/742* (2013.01); *A61B 5/7425* (2013.01); *A61B 6/5247* (2013.01); *G02B 5/208* (2013.01); *H01L 27/1462* (2013.01); *H01L 27/14625* (2013.01); *H01L 27/14627* (2013.01); *H01L 27/14634* (2013.01); *H01L 27/14645* (2013.01); *H01L 27/14649* (2013.01); *H04N 5/2254* (2013.01); *H04N 5/2256* (2013.01); *H04N 5/2258* (2013.01); *H04N 5/23293* (2013.01); *H04N 5/369* (2013.01); *A61B 5/6833* (2013.01); *A61B 2560/0431* (2013.01); *A61B 2562/0238* (2013.01); *A61B 2562/046* (2013.01); *A61B 2562/146* (2013.01); *G02B 27/286* (2013.01); *H04N 5/374* (2013.01); *H04N 9/045* (2013.01); *H04N 9/09* (2013.01)

(58) Field of Classification Search
CPC ... A61B 5/7425; H04N 5/2256; G01J 3/2803; G01J 3/36; G01J 2003/1226; G01J 2003/2826; G01J 2005/0077; G01J 3/02; G01J 3/0208; G01J 3/0232; G01J 3/0237; G01J 3/0256; G01J 3/0264
USPC .......................................................... 348/164
See application file for complete search history.

(56) References Cited

U.S. PATENT DOCUMENTS

| 2009/0309960 A1* | 12/2009 | Park | G01J 3/0208 348/61 |
| 2011/0102392 A1* | 5/2011 | Fujioka | G02F 1/13338 345/207 |
| 2017/0026588 A1* | 1/2017 | Kester | G01J 5/0014 |

* cited by examiner

*Primary Examiner* — Masum Billah

(57) ABSTRACT

A portable multispectral imaging device comprises a first image sensing module, including at least one lens module and an image sensor. The image sensor is configured to acquire a plurality of images of light radiation, passing through the lens module, and the images include at least one first visible light image and an invisible light image. The center of the lens module and the center of the image sensor are aligned on an optical axis. Moreover, a plurality of light sources including at least one invisible light source are arranged to surround the first image sensing module. A flat-panel display module configured to show an image including the acquired images and previously saved images.

5 Claims, 16 Drawing Sheets

(51) Int. Cl.
*G02B 5/20* (2006.01)
*A61B 5/103* (2006.01)
*A61B 6/00* (2006.01)
*H04N 5/232* (2006.01)
G02B 27/28 (2006.01)
H04N 5/374 (2011.01)
H04N 9/04 (2006.01)
H04N 9/09 (2006.01)

PORTABLE MULTISPECTRAL IMAGING DEVICE AND METHOD OF REDUCING INTERFERENCE OF DISPLAYED IMAGES THEREOF

CROSS REFERENCE

This application is based upon and claims the benefit of priority of Chinese Patent Applications No. 201710202248.X, filed on Mar. 30, 2017, and No. 201710202019.8, filed on Mar. 30, 2017, the entire contents thereof are incorporated herein by reference.

TECHNICAL FIELD

The present disclosure relates to the field of locating blood vessels, specifically to a portable multispectral imaging device and a method of reducing interference of displayed images of blood vessels thereof.

BACKGROUND

Subcutaneous structures and blood vessels under skin are barely visible for naked eyes. In order to identify and locate the subcutaneous structures and blood vessels, medical doctors have to rely on the external outline of human body and their anatomic knowledge.

The blood vessels, including veins and arteries, are below the epidermis, and even covered by subcutaneous fat. Visible light imaging signals, reflected back from subcutaneous structures and blood vessels under the visible light illumination, are extremely faint and mixed with scattered light and various phantoms. Before puncturing, in order to make the blood vessels more visible, medical doctors often ask patients to clench their fists or flap the skin above the blood vessel. However, the visibility of subcutaneous blood vessels is still not satisfied in most cases accompany with ages, or thickness of subcutaneous fat of patients. Injection relying on the vague images of blood vessels often results misalignment of the puncture, causing pain in patients, delaying optimal time for medical treatments, and even triggering injection incident.

In addition to drawing blood and injections in various occasions, blood vessels are also needed to be accurately located during acupuncture and medical surgeries.

An existing vein image enhancer, projects the acquired near-infrared (NIR) image of the venous blood vessels, by the visible light, directly onto the skin surface of a human body. However, the existing vein image enhancer is not able to show the subcutaneous structures and blood vessels together and have enormous volume and huge power consumption, which is not suitable for mobile medical diagnosis and treatments.

SUMMARY

The primary purpose, of the present disclosure is to provide a portable multispectral imaging device and a method of acquiring images of blood vessels and subcutaneous structures thereof. The portable multispectral imaging device is capable of capturing infrared images, and displaying the acquired image information, e.g. invisible light image information and visible light image information, with other information, e.g. X-ray image information. Therefore, the medical doctors are able to accurately detect the positions of subcutaneous structures and blood vessels which allow the medical doctors to have sufficient information for applying diagnosis and treatments.

In one embodiment of the present disclosure, a portable multispectral imaging device includes a first image sensing module including at least one lens module and an image sensor, a plurality of light sources including at least one invisible light source, and a flat-panel display module.

The image sensor is configured to acquire a plurality of multispectral images of light radiation, passing through the lens module, wherein the multispectral images include at least one first visible light image and an invisible light image.

The center of the lens module and a center of the image sensor are aligned on an optical axis. The light sources are arranged to surround the first image sensing module. The flat-panel display module is configured to display an image includes the acquired visible and invisible images and previously saved images.

In one embodiment of the present disclosure, a method of reducing interferences of images displayed by a portable multispectral imaging device is provided. The method comprises steps of illuminating, by a plurality of light sources including at least one invisible light source, a plurality of light radiations including at least one invisible light radiation; acquiring, by an image sensor of a first image sensing module including at least one lens module, a plurality of images of light radiation, passing through the lens module, and the acquired images include at least one first visible light image and an invisible light image; and displaying, by a flat-panel display module, an image includes the acquired images and previously saved images. Moreover, image acquisition is occurred when the light sources are turned on, and the flat-panel display shows images when the light sources are turned off.

BRIEF DESCRIPTION OF THE DRAWINGS

Embodiments of the present disclosure will now be described, by way of example only, with reference to the accompanying schematic drawings in which corresponding reference symbols indicate corresponding parts, and in which.

DETAILED DESCRIPTION

In the following, embodiments of the present disclosure will be described in detail referring to figures. The concept and its realizations of the present disclosure can be implemented in a plurality of forms, and should not be understood to be limited to the embodiments described hereafter. In contrary, these embodiments are provided to make the present disclosure more comprehensive and understandable, and so the conception of the embodiments can be conveyed to the technicians in the art fully. Same reference signs in the figures refer to same or similar structures, so repeated description of them will be omitted.

The features, structures or characteristics described can be combined in any appropriate way in one or more embodiments. In the description below, many specific details are provided to explain the embodiments of the present disclosure fully. However, the technicians in the art should realize that, without one or more of the specific details, or adopting other methods, components, materials etc., the technical proposal of the present disclosure can still be realized. In certain conditions, structures, materials or operations well known are not shown or described in detail so as not to obfuscate the present disclosure.

The technical contents of the present disclosure will be further described below with reference to the figures and embodiments.

It should be stated that a plurality of embodiments described below along with their combinations and varieties, beyond doubt are within the scope of the present disclosure.

Figure 1:
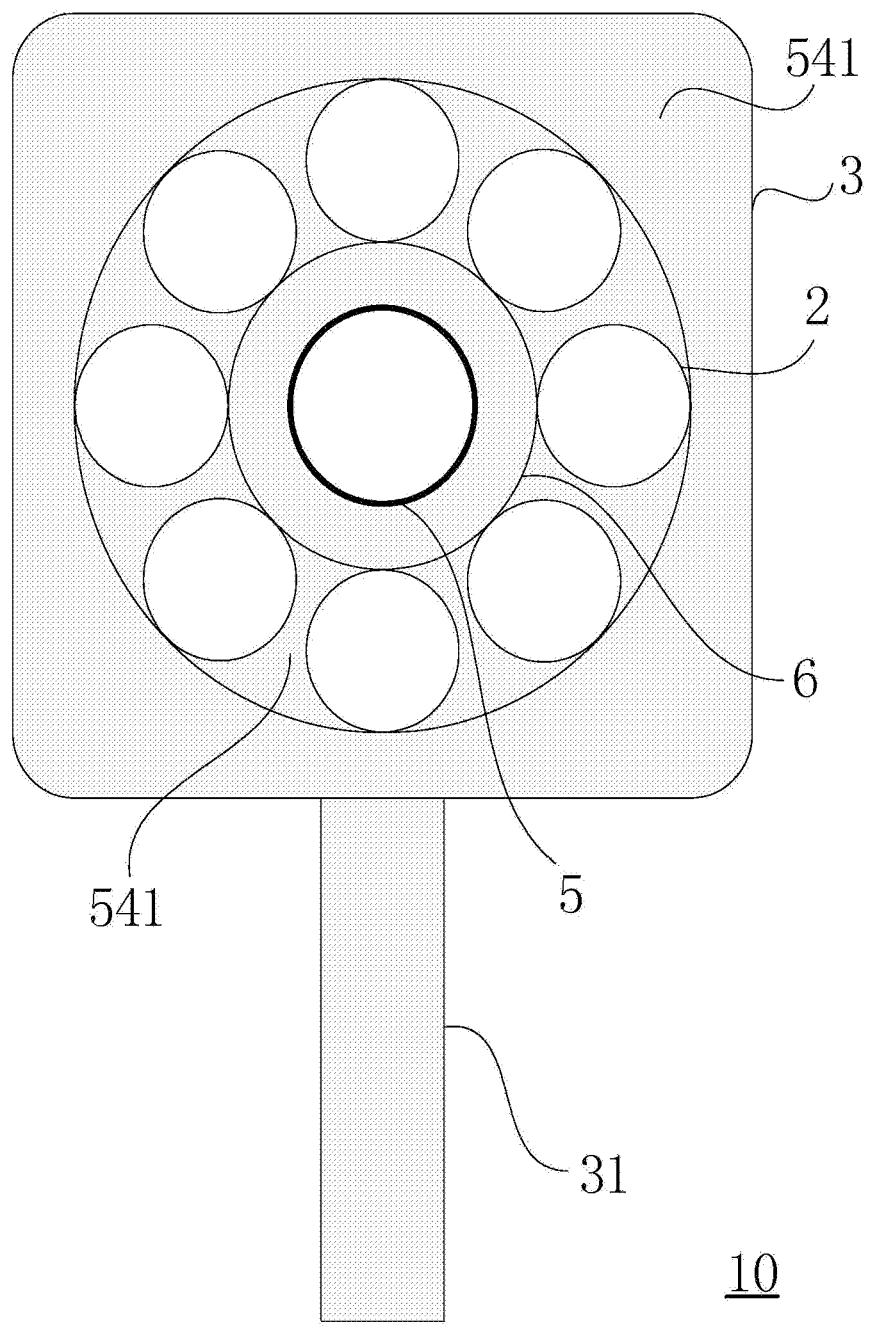
FIG. 1 shows a schematic front view of a portable multispectral imaging device of one embodiment of the present disclosure.
Figure 2:
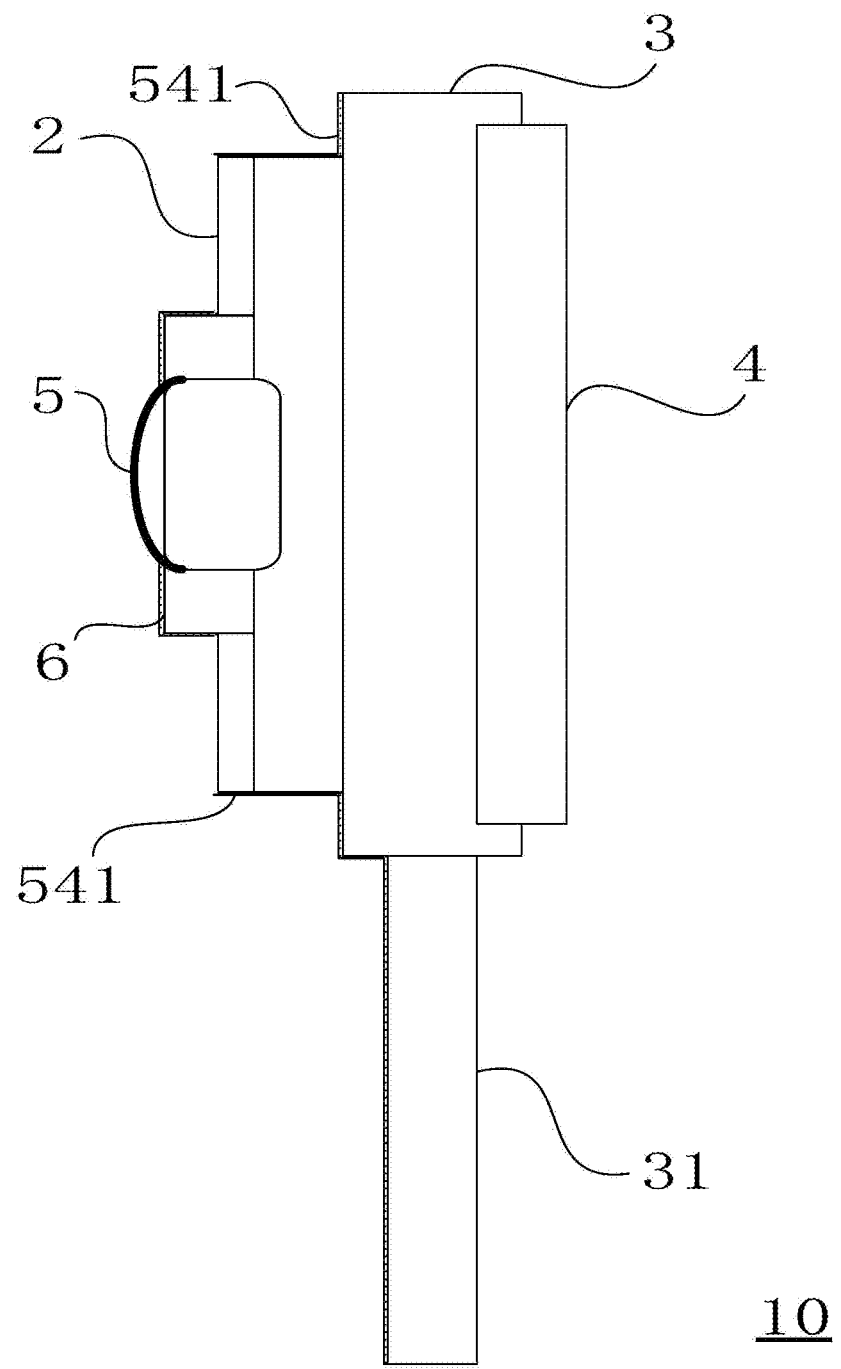
FIG. 2 shows a schematic cross sectional view of the portable multispectral imaging device of FIG. 1.

FIG. 1 shows a front view of a portable multispectral imaging device 10 of one embodiment of the present disclosure. FIG. 2 shows a cross sectional view of the portable multispectral imaging device 10 of FIG. 1. As shown in FIG. 1, in this embodiment, the portable multispectral imaging device 10 includes a main body 3 and a handler 31 coupled to the main body 3.

In this embodiment, as shown in FIGS. 1 and 2, the main body 3 includes a first image sensing module 5, a plurality of light sources 2 including at least one invisible light source, a light-absorbing plateau 6 disposed on a first side of the main body 3, and a flat-panel display module 4 disposed on a second side of the main body 3. In this embodiment, as shown in FIG. 2, the first side of the main body 3 is opposite to the second side of the main body 3.

The light sources 2, as shown in FIG. 1, are arranged to surround the first image sensing module 5 and are configured to illuminate a plurality of visible light and at least one invisible light onto skin of an organism, e.g. human, having blood vessels. In this embodiment, the visible light includes white light illuminated by LEDs (Light Emitting Diodes) and the invisible light includes infrared. The invisible light includes a wavelength in a range of 0.76 microns to 10 microns.

In some embodiments, as shown in FIGS. 1 and 2, the portable multispectral imaging device 10 further includes a light absorbing material 541 coated on surface of the main body 3 and the handler 31 without blocking light illuminating of the light sources 2 and light receipts of the first image sensing module 5.

Figure 3:
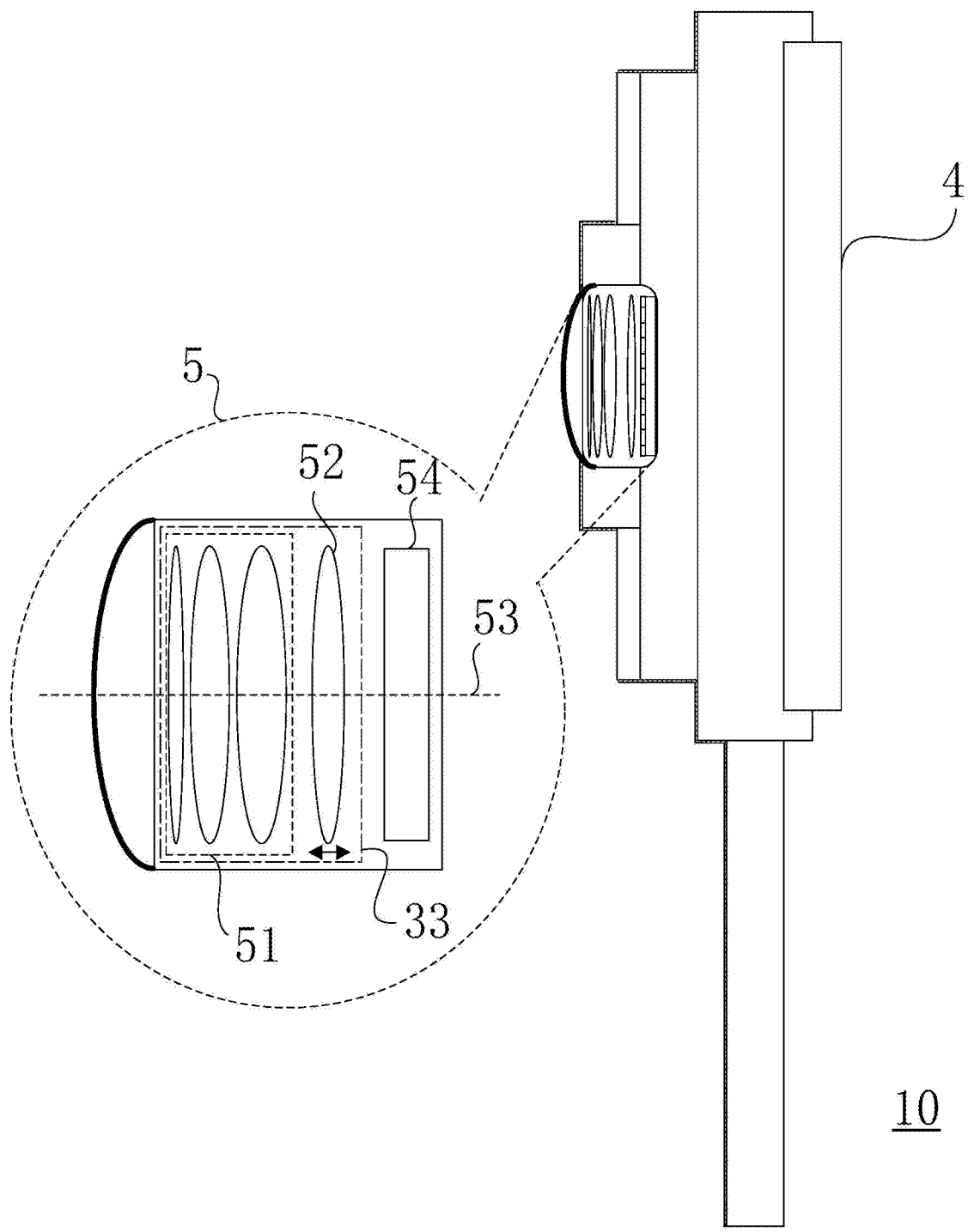
FIG. 3 shows a schematic cross sectional view of a first image sensing module of the portable multispectral imaging device of one embodiment of the present disclosure.

FIG. 3 shows schematic a cross sectional view of a first image sensing module 5 of the portable multispectral imaging device 10 of one embodiment of the present disclosure. In this embodiment, as shown in FIG. 3, the first image sensing module 5 includes at least one lens module 33, and an image sensor 54. Moreover, the lens module 33 includes a plurality of objective lenses 51 and a focusing lens 52. As shown in FIG. 3, the focusing lens 52 is configured to focus light radiation, passing through the objective lenses 51, to the image sensor 54. In some embodiments, the flat-panel display 4 includes a LED (Light Emitting Diode) display. In some embodiments, the image sensing sensor 54 includes a CCD (Charge-coupled Device). In some embodiments, the image sensor 54 includes a CMOS (Complementary Metal Oxide Semiconductor).

The image sensor 54 is configured to acquire a plurality of multispectral images of the light radiation, passing through the focusing lens 52, and the multispectral images include at least one first visible light image and a first invisible light image. In this embodiment, the center of the lenses 51 and 52, and the center of the image sensor 54 are aligned on an optical axis 53.

Figure 4:
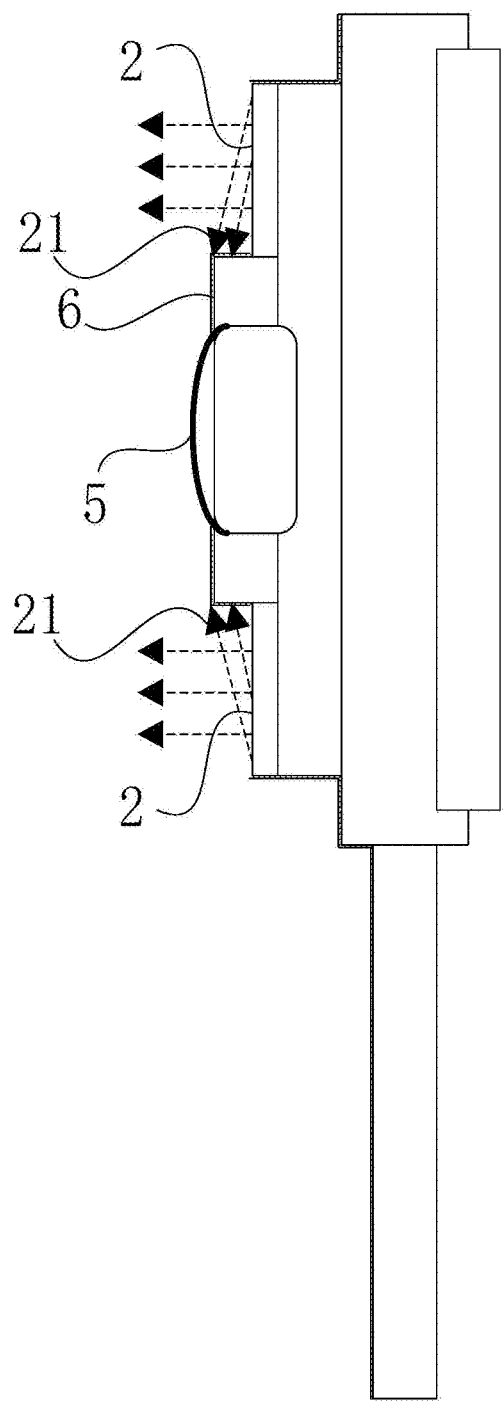
FIG. 4 shows a schematic view of light paths of a plurality of light sources of the portable multispectral imaging device of one embodiment of the present disclosure.

FIG. 4 shows a schematic view of light paths of a plurality of light sources 2 of the portable multispectral imaging device 10 of one embodiment of the present disclosure. As shown in FIG. 4, in this embodiment, the light-absorbing plateau 6 is disposed between the first image sensing module 5, and the light sources 2. Moreover, as shown in FIG. 4, the light-absorbing plateau 6 further includes a step structure or a wall structure, which blocks direct light-paths 21 between the light sources 2 and the first image sensing module 5 for improving the image quality including contrast and brightness of images displayed by the flat-panel display module 4.

Figure 5:
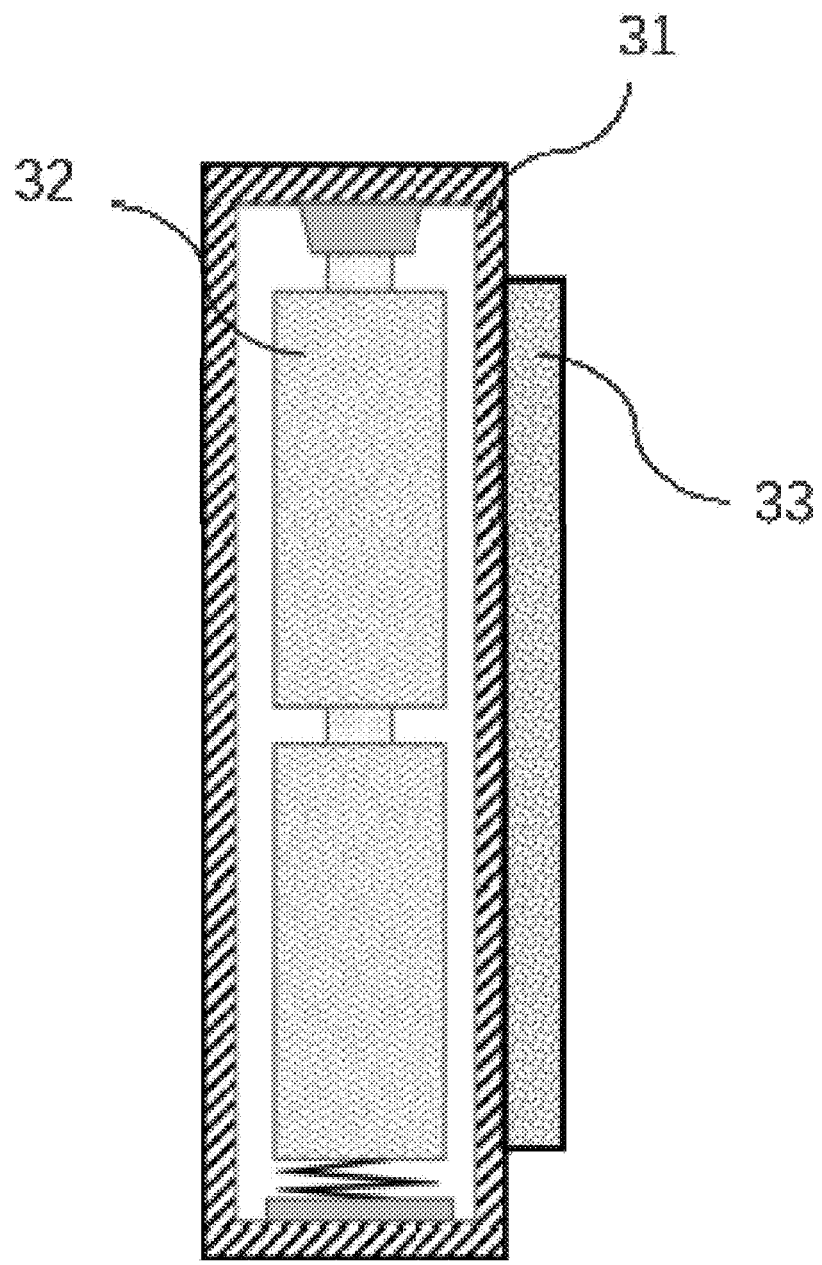
FIG. 5 shows a schematic cross-sectional view of a handler of a portable multispectral imaging device of FIG. 1.
Figure 6:
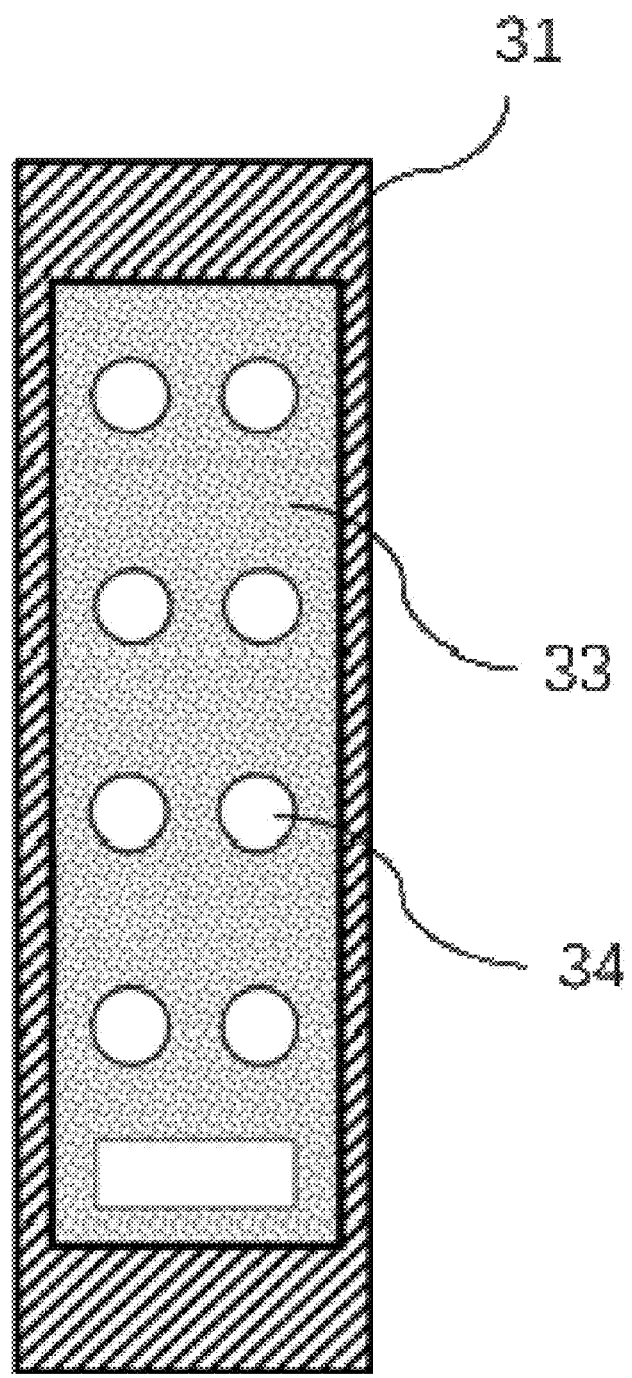
FIG. 6 shows a schematic view of a control panel of the handler of FIG. 5.

FIG. 5 shows a schematic cross-sectional view of a handler of a portable multispectral imaging device of FIG. 1. FIG. 6 shows a schematic view of a control panel of the handler of FIG. 5. As shown in FIGS. 5 and 6, the handler 31 includes a space for receiving power modules 32, e.g. batteries, and control circuits (not shown). The power modules 32 are coupled to the control circuits and provide operating power to the portable multispectral imaging device 10.

Moreover, the handler 31 further includes a control panel 33 with a plurality of control buttons 34 coupled to the control circuit, which allow users to operate the portable multispectral imaging device. Furthermore, in some embodiments, the handler 31 is coupled to the main body with a revolving platform (not shown).

Figure 7:
FIG. 7 shows a schematic view of the portable multispectral imaging device displaying an image including the acquired visible and invisible images and previously saved images one embodiment of the present disclosure.

FIG. 7 shows a schematic view of the portable multispectral imaging device displaying an image including the acquired visible and invisible images and previously saved images one embodiment of the present disclosure. As shown in FIG. 7, the image is displayed by the flat-panel display module 4 of the portable multispectral imaging device 10 of FIG. 1. In this embodiment, an infrared image 71, e.g. a blood vessel image, is a real time image of the object and is displayed with a previously saved image 73 of the object, e.g. an X-ray bone image.

Figure 8:
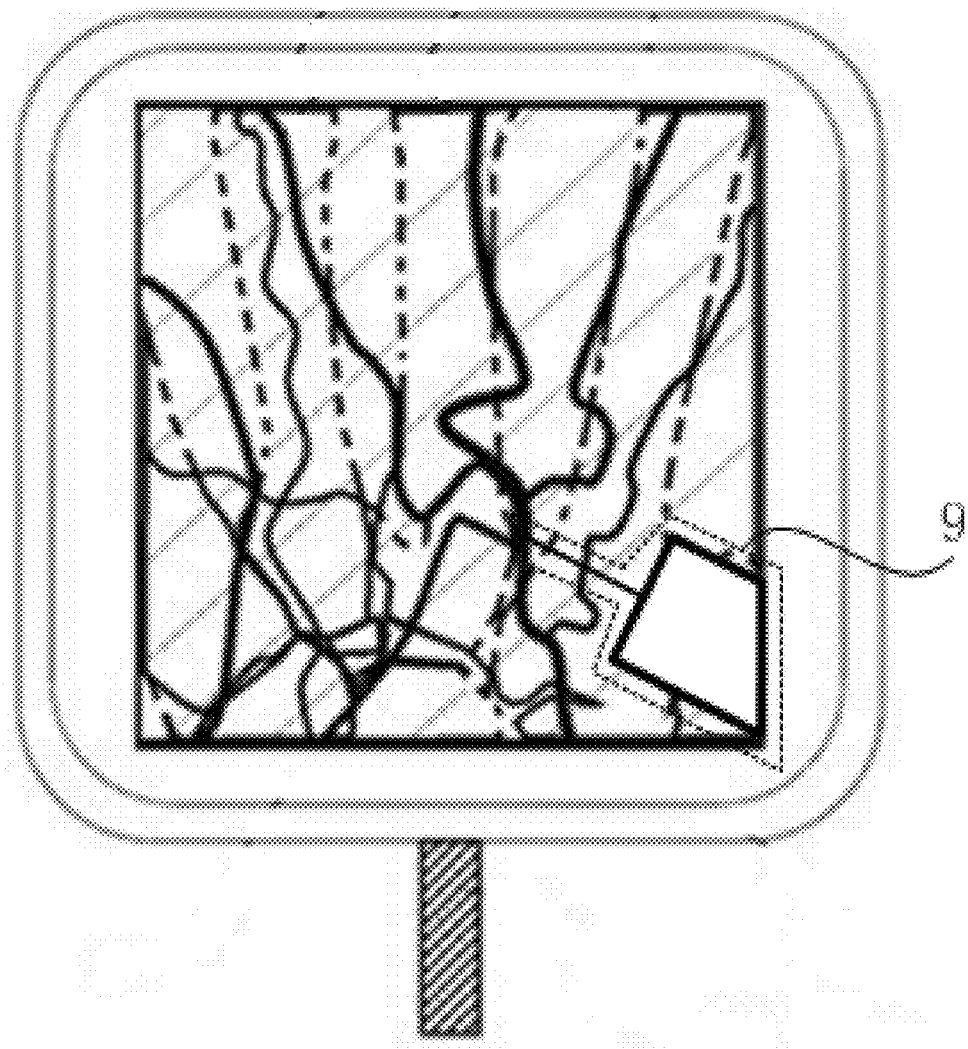
FIG. 8 shows a schematic view of an image displayed by a flat-panel display module of the portable multispectral imaging device of one embodiment of the present disclosure.

Therefore, in this embodiment, during medical exam, the locations of blood vessels and bones can be identified, which allow the users to accurately apply medical treatments, e. g. injection, as shown in FIG. 8. Moreover, in this embodiment, the second invisible light 73 includes a wavelength in a range of 0.01 nanometers to 10 nanometers. As shown in FIG. 8, in this embodiment, the user is applying injection with a syringe 9.

Figure 9:
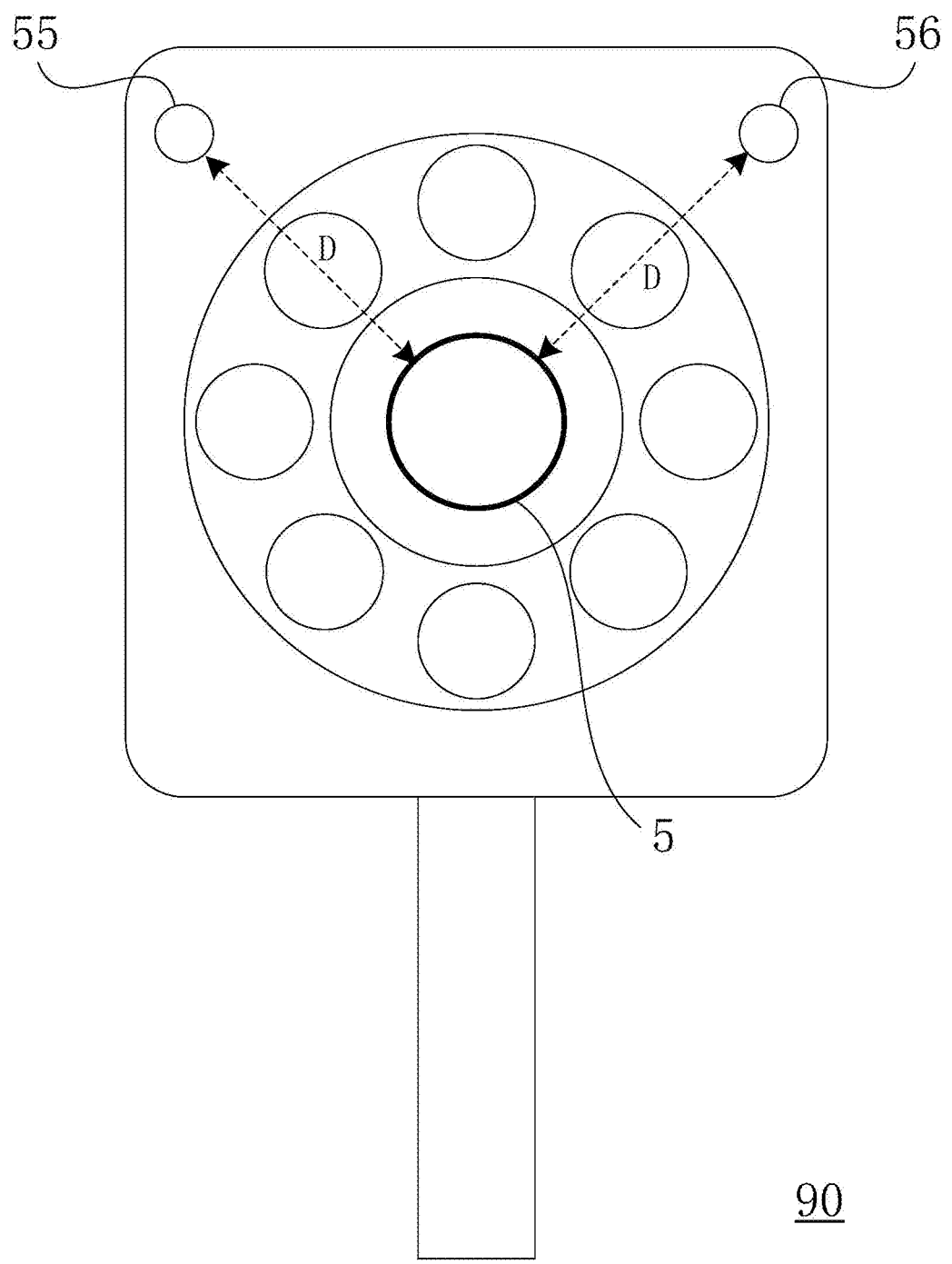
FIG. 9 shows a schematic front view of another portable multispectral imaging device of one embodiment of the present disclosure.
Figure 10:
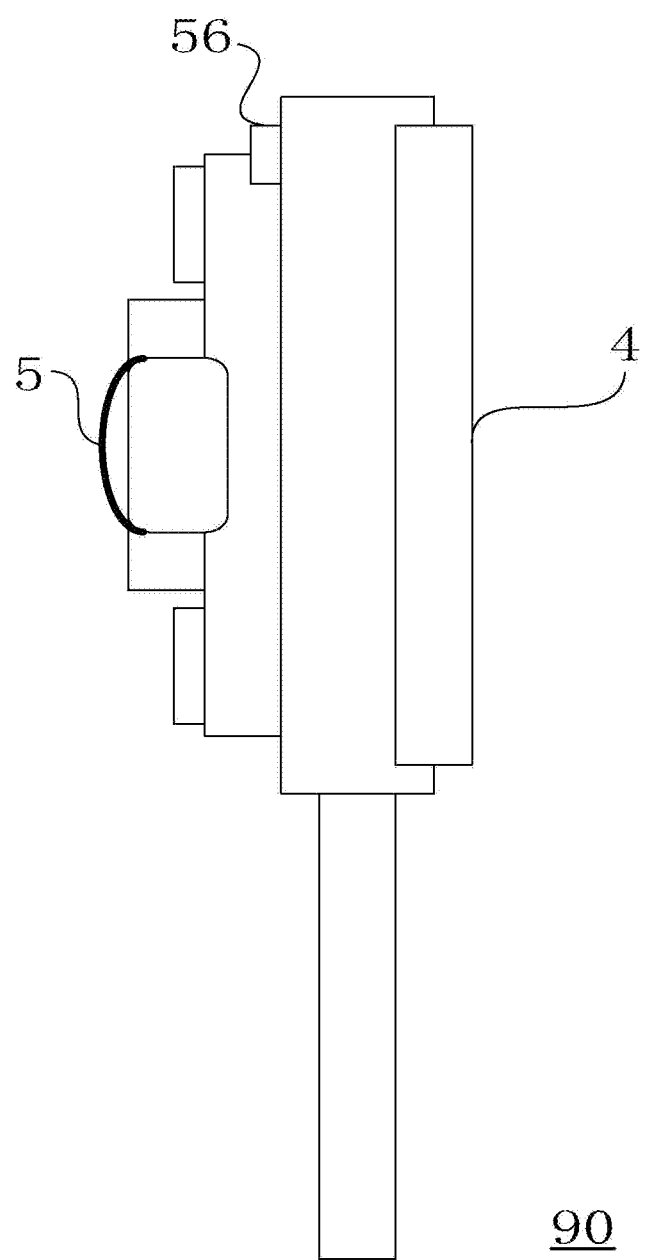
FIG. 10 shows a schematic cross sectional view of the portable multispectral imaging device in FIG. 9.

FIG. 9 shows a schematic front view of a portable multispectral imaging device 90 of one embodiment of the present disclosure. FIG. 10 shows a schematic cross sectional view of the portable multispectral imaging device 90 of FIG. 9. As shown in FIGS. 9 and 10, in this embodiment, the portable multispectral imaging device 90 is similar to the portable multispectral imaging device 10 of FIG. 1 but further includes a second image sensing module 55 and a third image sensing module 56. Moreover, in this embodiment, the second image sensing module 55 and the third image sensing module 56 are respectively and equally distant from the first image sensing module 5 with a distance "D".

The second image sensing module 55 is configured to acquire a second visible light image, and the third image sensing module 56 is configured to acquire a third visible light image. Therefore, an image, displayed by the flat-panel display module 4, includes the first visible light image, the second visible light image, the third visible light image, the first invisible light image, and the previously saved images. In some embodiments, the flat-panel display module 4 is configured to show three-dimensional image information, which is generated in response to a plurality of multispectral images respectively acquired by imaging sensing module 5, imaging sensing module 55 and imaging sensing module 56.

Figure 11:
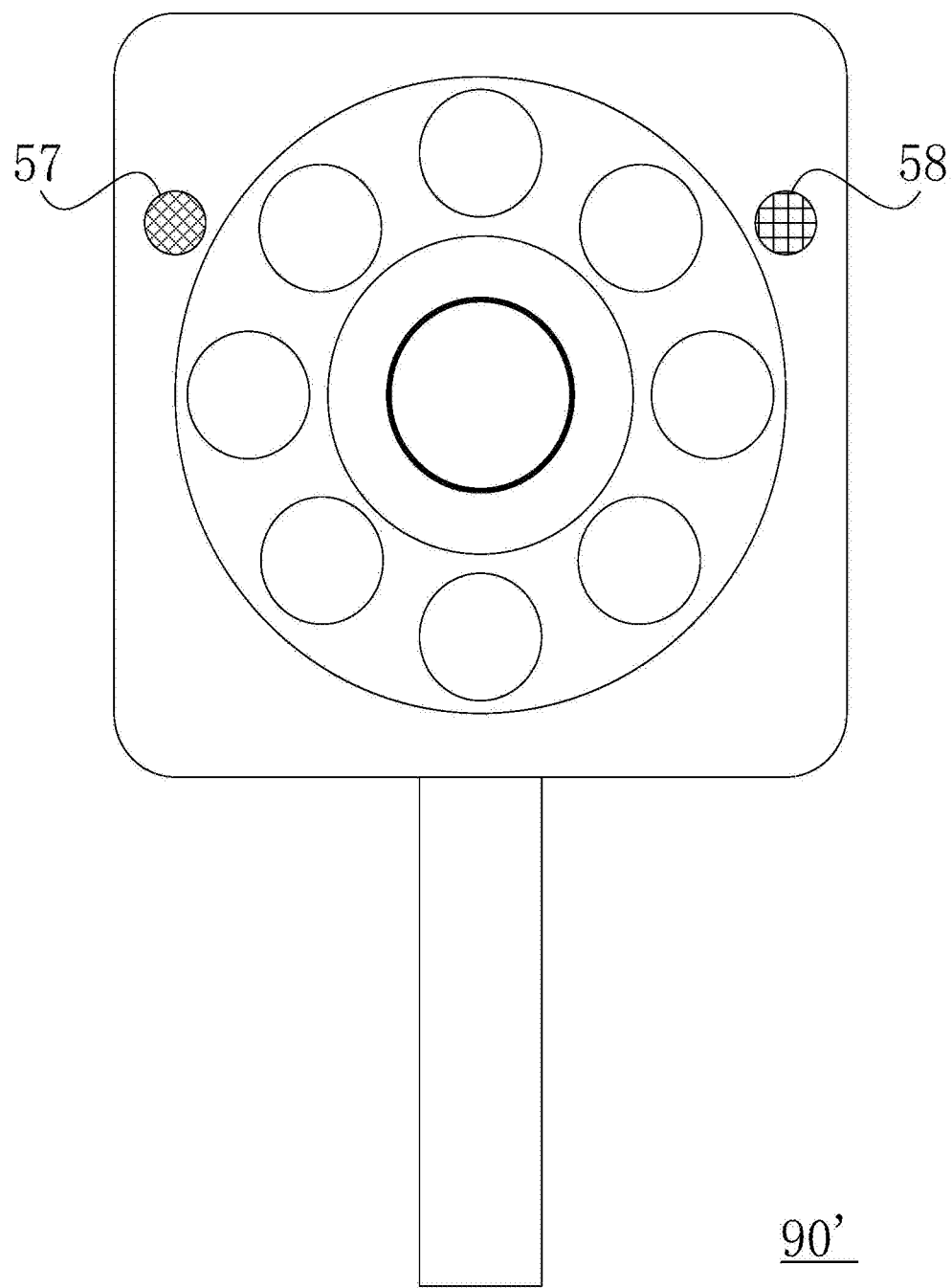
FIG. 11 shows a schematic front view of a portable multispectral imaging device of one embodiment of the present disclosure.

FIG. 11 shows a schematic front view of a portable multispectral imaging device of one embodiment of the present disclosure. As shown in FIG. 11, in this embodiment, the portable multispectral imaging device 90' is similar to the portable multispectral imaging device 90 of FIG. 9, but includes a second image sensing module 57 configured to acquire a color image information of the visible light, and a third image sensing module 58 configured to acquire a black-and-white image information of the visible light. Therefore, an image, displayed by the flat-panel display module, is generated in response to the first visible light image, the color image information of the visible light, the black-and-white image information of the visible light, the invisible light image, and the previously saved image.

Figure 12:
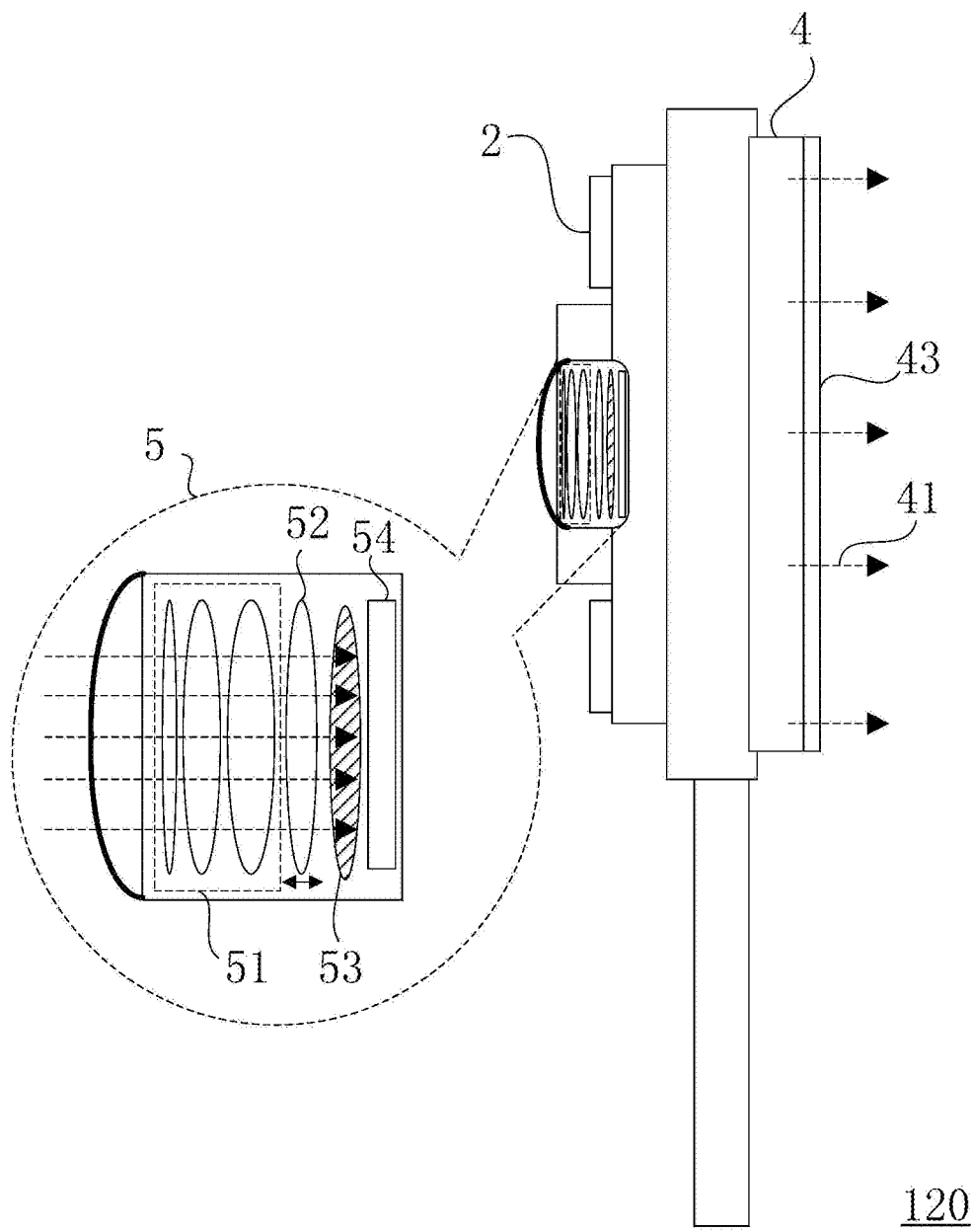
FIG. 12 shows a schematic view of a portable multispectral imaging device of one embodiment of the present disclosure.
Figure 13:
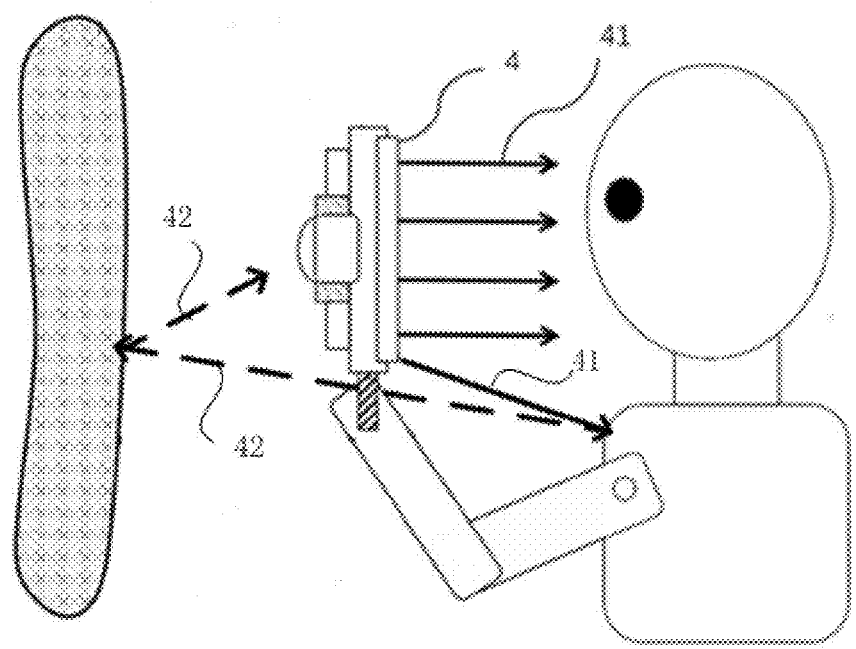
FIG. 13 shows a schematic view of the portable multispectral imaging device of FIG. 12.

FIG. 12 shows a schematic view of a portable multispectral imaging device 120 of one embodiment of the present disclosure. FIG. 13 shows a schematic view of the portable multispectral imaging device 120 of FIG. 12.

As shown in FIGS. 12 and 13, in order to reduce stray light interference, caused by a reflected or a scattered light 42 of the visible light 41 that is emitted by the flat-panel display module 4, the portable multispectral imaging device 120 further includes a first polarizing film 43 disposed on the light-output side of the flat-panel display 4 and a second polarizing film 53 disposed on the light-input side of the image sensor 54. Moreover, in this embodiment, the polarization direction of the first polarizing film 43 is orthogonal to the polarization direction of the second polarizing film 53, in order to prevent the reflected light 42 entering into the imaging sensor 54.

Figure 14:
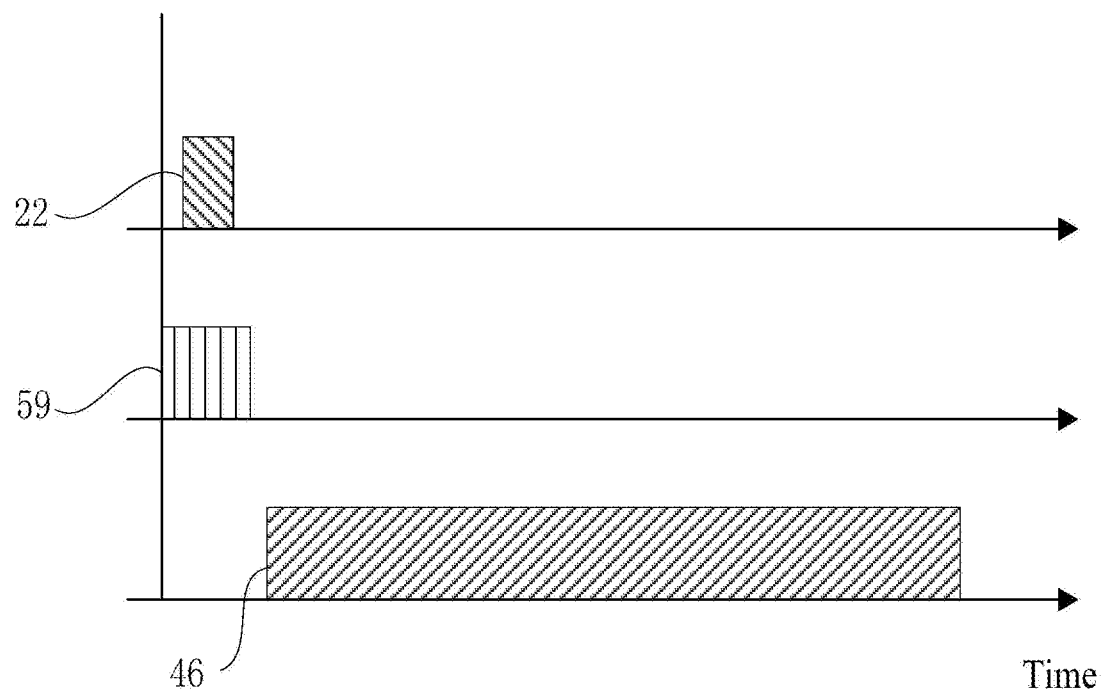
FIG. 14 shows an operational time sequence of the portable multispectral imaging device of one embodiment of the present disclosure.

FIG. 14 shows an operational time sequence of the portable multispectral imaging device 10 of FIGS. 1 to 3, as shown in FIG. 14, an illuminating time pulse 22 represents the illumination time of the light sources 2, an image acquisition pulse 59 represents the image acquisition time of imaging sensor 54, and an image displaying pulse 46 represents the display time of the flat-panel display 4.

In order to minimize stray light interferences, in some other embodiments, an arrangement of the time sequence, as shown in FIG. 14, is implemented. In this embodiment, image acquisition is occurred, as indicated by the image acquisition pulse 59, in response to an illuminating time pulse 22 of the light source, and the image displaying pulse 46 is activated in response to a non-illuminating time of the light source. In some embodiments, the pulse width of the image acquisition pulse 59 is longer than or equal to the pulse width of the illuminating time pulse 22 of the light source, in order to acquire at least two images, one with and one without illumination of light source. Subtraction of image data without illumination of light source will further minimize interference of environment light.

Figure 15:
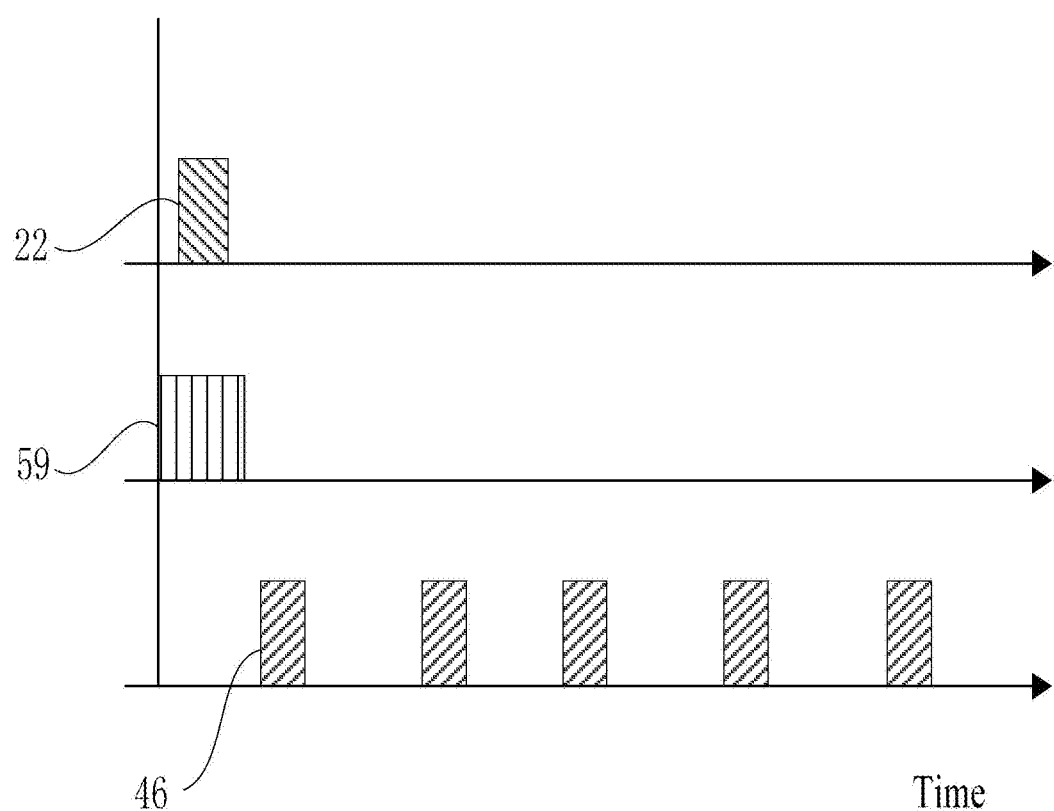
FIG. 15 shows an operational time sequence of the portable multispectral imaging device of one embodiment of the present disclosure.

Time sequence, as shown in FIG. 14, may result in display flickering, since the display light is turned off during the image acquisition time 59. As illustrated in FIG. 15, an embodiment is similar to the embodiment of FIG. 14 but the image displaying pulses 46, generated by light sources of the display, e.g. LEDs in the display backlight unit, are flashing in a frequency much higher than the limit, e.g. 120 Hz, that human retina can response. The display flickering is then barely visible to human's naked eyes.

Figure 16:
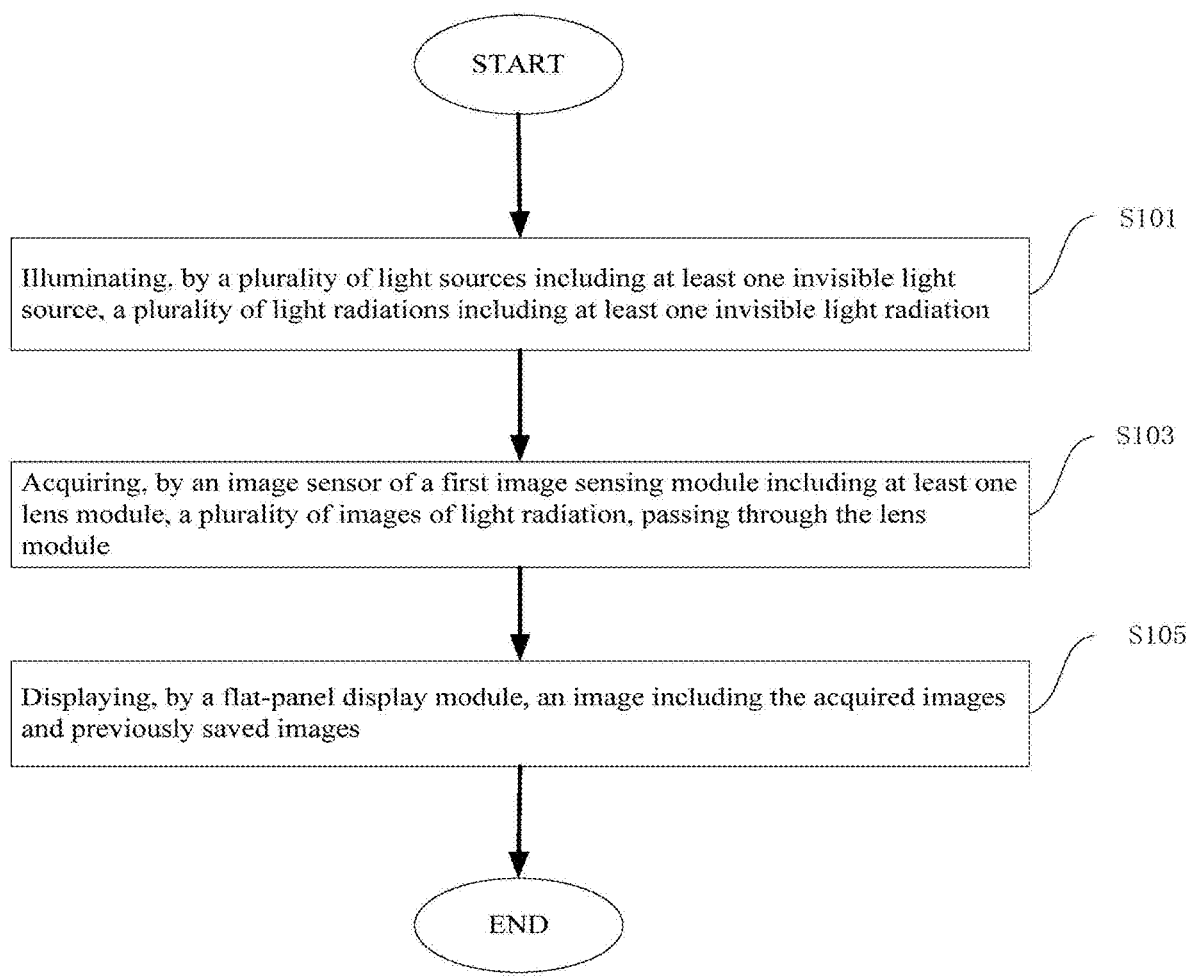
FIG. 16 shows a flow chart of a method of reducing interferences of images displayed by a portable multispectral imaging device of one embodiment of the present disclosure.

FIG. 16 shows a flow chart of a method of reducing interferences of images displayed by a portable multispectral imaging device of one embodiment of the present disclosure. As shown in FIG. 16, in step S101, a plurality of light radiations including at least one invisible light radiation are illuminated by a plurality of light sources including at least one invisible light source of the portable multispectral imaging device. In step S103, a plurality of images of light radiation, passing at least one lens module, is acquired by an image sensor of a first image sensing module including the at least one lens module of the portable multispectral imaging device.

In this embodiment, the images of the light radiation include at least one first visible light image and an invisible light image.

In step S105, an image including the acquired images and previously saved images are displayed by a flat-panel display module of the portable multispectral imaging device. In this embodiment, image acquisition is occurred when the light sources are turned on, and the flat-panel display shows images when the light sources are turned off.

What is claimed is:
1. A portable multispectral imaging device, comprising:
an image sensing module, including one lens module and an image sensor, wherein the image sensor is configured to acquire a plurality of multispectral images of light radiation, passing through the lens module, and the multispectral images include at least one first visible light image and a first invisible light image, and the center of the lens module and the center of the image sensor are aligned on an optical axis;

a plurality of light sources including at least one invisible light source, wherein the light sources are arranged to surround the image sensing module;

a flat-panel display shows an image includes acquired visible and invisible light images, and previously saved images;

the invisible light source includes infrared and the infrared includes a wavelength in a range of 0.76 microns to 10 microns; and the image sensing module includes a first polarizing film disposed on the light-output side of the flat-panel display and a second polarizing film disposed on the light-input side of the image sensor, wherein polarization direction of the first polarizing film is orthogonal to the polarization direction of the second polarizing film.

2. The portable multispectral imaging device of claim 1, wherein image acquisition occurs when the light sources are turned on, and the flat-panel display shows images when the light sources are turned off.

3. The portable multispectral imaging device of claim 1, wherein the previously saved images include X-ray images and the X-ray wavelength is in a range of 0.01 nanometers to 10 nanometers.

4. The portable multispectral imaging device of claim 1, wherein the image sensor includes a CMOS (Complementary Metal Oxide Semiconductor).

5. A method of reducing interferences of images displayed by a portable multispectral imaging device, the method comprising steps of:

illuminating, by a plurality of light sources including at least one invisible light source, a plurality of light radiations including at least one invisible light radiation;

acquiring, by an image sensor of an image sensing module including one lens module, a plurality of images of light radiation, passing through the lens module, wherein the images of the light radiation includes at least one first visible light image and an invisible light image; and displaying, by a flat-panel display module, an image including acquired images and previously saved images;

the invisible light source includes infrared and the infrared includes a wavelength in a range of 0.76 microns to 10 microns;

wherein image acquisition is occurred when the light sources are turned on, and the flat-panel display shows images when the light sources are turned off; and the image sensing module includes a first polarizing film disposed on the light-output side of the flat-panel display and a second polarizing film disposed on the light-input side of the image sensor, wherein polarization direction of the first polarizing film is orthogonal to the polarization direction of the second polarizing film.

* * * * *